United States Patent
Martin

(10) Patent No.: US 8,257,655 B2
(45) Date of Patent: Sep. 4, 2012

(54) GAS DETECTING ARRANGEMENT

(75) Inventor: Hans Göran Evald Martin, Delsbo (SE)

(73) Assignee: Senseair AB, Delsbo (SE)

( * ) Notice: Subject to any disclaimer, the term of this patent is extended or adjusted under 35 U.S.C. 154(b) by 568 days.

(21) Appl. No.: 11/794,460

(22) PCT Filed: Dec. 8, 2005

(86) PCT No.: PCT/SE2005/001871
§ 371 (c)(1), (2), (4) Date: Jun. 28, 2007

(87) PCT Pub. No.: WO2006/071171
PCT Pub. Date: Jul. 6, 2006

(65) Prior Publication Data
US 2008/0019877 A1 Jan. 24, 2008

(30) Foreign Application Priority Data
Dec. 29, 2004 (SE) ....................... 0403195

(51) Int. Cl.
*G01N 33/00* (2006.01)
(52) U.S. Cl. ...................... 422/83; 422/82.05
(58) Field of Classification Search ............... 422/83, 422/82.05; 356/437
See application file for complete search history.

(56) References Cited

U.S. PATENT DOCUMENTS

| 5,489,457 | A | * | 2/1996 | Vent ............................. 428/40.9 |
| 5,599,503 | A | * | 2/1997 | Manz et al. ................. 422/82.05 |
| 5,874,737 | A | * | 2/1999 | Bytyn et al. ................... 250/343 |
| 5,932,877 | A | | 8/1999 | Braig et al. |
| 6,067,840 | A | | 5/2000 | Chelvayohan et al. |
| 2002/0062070 | A1 | | 5/2002 | Tschupp et al. |

FOREIGN PATENT DOCUMENTS

| DE | 197 39 722 A1 | 4/1999 |
| EP | 0 704 691 A2 | 4/1996 |
| GB | 2 392 721 A | 10/2004 |
| JP | 64-013439 A | 1/1989 |
| JP | 04-268437 A | 9/1992 |
| JP | 6-84937 B2 | 10/1994 |
| JP | 08-193952 A | 7/1996 |
| WO | WO-01/25137 A1 | 4/2001 |
| WO | WO-01/81900 A1 | 11/2001 |
| WO | 2005/059524 A1 | 6/2005 |

\* cited by examiner

*Primary Examiner* — Sam P Siefke
(74) *Attorney, Agent, or Firm* — Drinker Biddle & Reath LLP

(57) ABSTRACT

The present invention relates to a gas detecting arrangement having a gas cell which includes a cavity, a gas-cell-related light source, a gas-cell-related light detector and a controlling and computing unit wherein the unit is adapted fro initiating activation of the light source and also to evaluate the presence and/or the concentration or a gas and/or a gas mixture enclosed in the cell cavity in response to light-detector-related signals received from the light detector.

17 Claims, 2 Drawing Sheets

GAS DETECTING ARRANGEMENT

FIELD OF THE INVENTION

The present invention relates generally to a gas detecting arrangement and more specifically to a gas detecting arrangement that comprises:

A. a gas cell that has an associated cavity and that includes in the gas cell and in the cavity one or more, preferably more or less, straight and/or reflected measuring paths:
B. a gas-cell related light source:
C. a gas-cell related light detector and/or light detectors and
D. a controlling and computing electronic unit.

The electronic unit, according to "D" above, is adapted, either directly or indirectly, to initiate activation of the light source via pulses and also to evaluate the presence of and/or a current concentration of a gas and/or gas mixture enclosed in the cell cavity, depending on the structure for receiving light-detector-related output signals from the light detector.

The main aim of the present invention is to minimize the structure of a gas or gas-mixture detecting arrangement and, in this regard, to provide an arrangement that is particularly adapted in relationship to a circuit board, card, or its like.

The invention is based on the concept that the cavity of the gas cell shall be related to a hard or a soft board or card that is related to a light source and/or to a light detector.

A practical application of the present invention is a board of the "printed circuit board type" or the type of printed circuit board on which board components are surface mounted, referred to hereinafter as a surface mounted board.

By "printed circuit board" is meant a board or a card on which there is printed electrical conductors that are co-ordinated in one or more layers to provide more or less complex conductor structures and conductive patterns By "surface-mounted circuit board" is meant a card or a "printed circuit board" that includes printed circuit conductors which, in one or more layers, co-ordinate a more or less complex conductor structure and printed circuit, where one or more discrete components may be surface mounted, such as via connecting wires soldered to surface-related connection pads or corresponding electric connectors.

Since the invention relates to a beneficial use of a hard or soft (flexible) board or card, and since these may be printed circuit boards or surface-mounted printed circuit boards that are appropriately structured or other kinds of circuit boards, for the sake of simplicity in respect of certain applications solely the term "board" will be used in the following description.

RELATED PUBLICATION

The International Patent Publication WO-A1-2005/059524, filed 19 Dec. 2003 as an International Patent Application under the Serial Number PCT/SE2003/002041, forms part of a related publication and in which is disclosed a fluid sensor.

This fluid sensor contains a fluid cell (1) adapted to enclose a volume of fluid (7), in the form of a gas or a liquid, that is to be analysed.

Said fluid sensor comprising an electromagnetic energy source (3) arranged to transmit electromagnetic waves (4) into the fluid cell (1) and at least one detector (5) to detect electromagnetic waves passing through the fluid cell (1) and at least one opening (2) for the inlet/outlet of a fluid that is to be analysed and a circuit board (8, 10 to 16) to evaluate the intensity of electromagnetic waves reaching said at least one detector (5) and/or to provide the circuitry for the electromagnetic energy source (3).

Said fluid sensor (1) is so formed that at least a part of the fluid cell (1) is incorporated into the substrate of the circuit board (8, 10 to 16).

It is further proposed that the fluid cell extends completely through the circuit board and/or across the circuit board or that the fluid cell is fully embedded in the substrate of the circuit board.

Further it is supposed that the fluid cell is built up of a plurality of circuit boards stacked together.

It is also suggested the use of the fluid sensor, within a medical equipment, for determining the concentration of carbon dioxide in the exhaled air of a person or person's breathing frequency, which means a risk that moister condensation collects on the inner walls of the gas cell, which deteriorated the quality of the signals passing through the gas cell and this can adversely affect the analysis results.

Said condensation effect may be avoided if electronic circuits, generating heat, are oriented adjacent to said fluid sensor or fluid cell.

BACKGROUND OF THE INVENTION

Several different methods and arrangements of the aforesaid nature and intended for the aforesaid application are known to the art.

By way of a first example of the background art and the technical field to which the present invention relates can be mentioned the possibility of constructing a requisite gas cell with an associated cavity having light reflecting wall portions as a separate unit and mounting this unit on a circuit board or on one surface of a surface-mounted circuit board, with the electronic circuits of a control unit being more or less related or a printed circuit board or to a surface-mounted circuit board.

It is also known to mount the light source and/or the light detector on one surface of a printed circuit board or of a surface-mounted circuit board and to form the gas cell with its cavity as a discrete component and to place this component between the light source and the light detector.

Also known to the prior art technology is a controlling and computing unit which includes a number of processor-controlled electronic circuits for executing a number of functions, among others the function of assessing the presence of and/or the concentration of a gas and/or a gas consistency by virtue of the wavelength and/or wavelengths of said gas absorbed during its passage through a measuring path in the cell in response to a signal structure obtained via the light detector in response to a generated pulsated light structure initiated via the light emitter.

Also belonging to the technology, to which the present invention relates, is an arrangement, taught by International Patent Publication WO-A1-01/81900.

This prior publication teaches an arrangement which is intended to be surface mounted on a printed circuit board or so-called surface-mounted board, where requisite circuit arrangements can be coordinated with surface mounted circuits and components.

As a part of the prior art, to be considered, is shown and described in the European Patent Application Serial Number 94 1 207 993.8 (EP-A2-0 704 691).

This patent publication discloses an Infra-Red Spectrometer Sensor for gases using micro-structure reflecting surfaces.

SUMMARY OF THE INVENTION

Technical Problems

When taking into consideration the technical deliberations that a person skilled in this particular art must make in order to provide a solution to one or more technical problems that he/she encounters, it will be seen that on the one hand it is necessary initially to realize the measures and/or the sequence of measures that must be undertaken to this end, and on the other hand to realize which means is/are are required in solving one ore more of these problems. On this basis, it will be evident that the technical problems listed below are highly relevant to the development of the present invention.

When considering the earlier standpoint of techniques described above it will be seen that a technical problem resides in the ability to realize the significance of, the advantages associated with and/or the technical measures and deliberations that are required in creating a gas cell cavity, that can be allocated an extremely small gas volume and therewith be able to create conditions for a rapid exchange of a first gas volume to be measured with a second new gas volume.

Another technical problem resides in the ability to realize the significance of, the advantages that are afforded by and/or the technical measures and deliberations that are required in order to form readily a gas-cell-related cavity that has a narrow elongated aperture in the form of a very small slot or a channel (the smallest possible related to the used light emitting means) in the board material.

Another technical problem resides in the ability to realize the significance of, the advantages that are afforded by and/or the technical measures and deliberations that are required to create a cavity where the beams of a light source can be concentrated through a small or narrow gap-shaped slot or a gap-shaped aperture, whose width corresponds to, or essentially corresponds to, a thickness (or a length) of a used incandescent filament and having at least light-reflecting wall portions situated opposite to a light detector and its particular light-sensitive part or chip section.

Another technical problem resides in the ability to realize the significance of, the advantages that are afforded by and/or the technical measures and deliberations that will be required in creating those conditions which will be required to co-ordinate and integrate completely or partially a very small and narrow gas detecting arrangement for a printed circuit board or component surface mounted board.

Another technical problem resides in the ability to realize the significance of, the advantages that are afforded by and/or the technical measures and deliberations that will be required in allowing a gas cell arrangement that includes requisite gas conducting connections to be included as a part of a constructed printed circuit board or a surface mounted board.

Another technical problem resides in the ability to realize the significance of, the advantages that are afforded by and/or the technical measures and deliberations that will be required in allowing said gas cell to be structured as a simple, small and straight or curved, slot-like or groove-like, aperture in the board, such as a printed circuit board or a board on which components are surface mounted, that has a longitudinally orientated narrow opening (less than 10 mm deep) in said board, wherein the narrow opening may be covered by a small covering element where the inner central surface part of said element may well have light reflecting properties.

Another technical problem resides in the ability to realize the significance of, the advantages that are afforded by and/or the technical measures and deliberations that will be required in allowing the opening to be structured as a slot and therewith adapted to pass completely through a board with at least two cover-functioning elements that may be placed on or applied to one or both sides of the board.

Another technical problem resides in the ability to realize the significance of, the advantages that are afforded by and/or the technical measures and deliberations that will be required in allowing said cover-functioning element to have the form of adhesive tape or a flexurally rigid element applied over the aperture opening and adhering to or fixed to or in some other way fastened to the outwardly exposable surface of a printed circuit board or a surface-mounted circuit board and, when necessary, ensuring that the surface of said cover element, facing towards and covering said aperture opening, includes light reflecting properties.

Another technical problem resides in the ability to realize the significance of, the advantages that are afforded by and/or the technical measures and deliberations that will be required in creating a smallest possible light beam conductor through a small aperture that has mutually opposing delimiting surfaces that have been adapted for and treated for high light reflecting purposes.

Another technical problem resides in the ability to realize the significance of, the advantages that are afforded by and/or the technical measures and deliberations that will be required in allowing said aperture to be connected to and/or formed directly as a wider light-source-adapted first opening than said aperture or slot in said board.

Another technical problem resides in the ability to realize the significance of, the advantages that are afforded by and/or the technical measures and deliberations that will be required in allowing said small or narrow slots, channels or apertures to be connected to and/or directly formed as a wider light-detector-adapted second opening than said small aperture or slot in said board.

Another technical problem resides in the ability to realize the significance of, the advantages afforded by and/or the technical measures and deliberations that will be needed in allowing said first wider opening to tightly surround a light emitting unit, whose electrical conducting lines may be orientated in respect to a printed circuit surface or to an opposing surface of a printed circuit board or to the opposing surface of a surface-mounted circuit board and each fastened to respective connecting pads orientated in relation to said electric connection lines.

Another technical problem resides in the ability to realize the significance of, the advantages afforded by and/or the technical measures and deliberations that will be needed in allowing said wider second opening to tightly surround a light detecting unit whose electrical connecting lines may be orientated with respect to and connected to respective connection pads on one surface of the printed circuit board or on mutually opposite surfaces of the printed circuit board with each of said connecting lines fastened to said pads orientated in relation to said lines.

Another technical problem is one that resides in the ability to realize the significance of, the advantages afforded by and/or the technical measures and deliberations that will be needed in further connecting said elongate cavity-forming small or narrow opening to one or more short gas-transporting slots or channels with the intention of enabling the first gas portion in said gas cell to be exchanged for a second gas portion.

Another technical problem resides in the ability to realize the significance of, the advantages afforded by and/or the technical measures and deliberations that will be required in allowing unit-associated electronic circuits to be co-ordinated, at least partially, with the circuits, patterns and discrete components of said printed circuit boards or component-surface-mounted boards.

Solution

The present invention relates to a gas detecting arrangement and takes it starting point from the known technology described in the introduction. This arrangement is designed to comprise a gas cell that includes a cavity, a gas-cell related light source, a gas-cell related light detector and a controlling and computing electronic unit.

Through the agency of circuits and functions, the electronic unit is adapted for initiating activation of said light source and is also adapted to evaluate the presence and/or the concentration of gas and/or a gas mixture enclosed in the cell cavity, in response to electric signals relating to and obtained from the light detector.

With the intention of solving one or more of the aforesaid technical problems, it is proposed, in accordance with the present invention, that the known technology is supplemented by allowing the gas cell to be structured with a small aperture in the form of a narrow slot or a narrow channel and/or a through-penetrating opening in the card or board used, such as a printed circuit board or component surface-mounted board and that an opening (or openings) assigned to said small aperture in said card or board is covered by one (or two) cover element, such as to enclose the gas transporting cavity.

By way of proposed embodiments, that all lie within the scope of the inventive concept, it is proposed that the small aperture in the form of a narrow channel shall be structured so as to pass entirely through the board with said covering element placed on one or both sides of the board.

The covering element may have the form of a piece of adhesive tape or the form of a flexurally rigid lid.

The small slot, channel or aperture may be connected directly to a first wider light source opening.

The small slot, channel or aperture will preferably be connected directly to a second wider opening relating to and matching a light detector.

The first wider opening may be adapted to tightly surround a light emitting unit with a narrow clearance, wherein connection lines may be orientated with regard with a board associated surface or opposing board surfaces and fastened to connection pads orientated with respect to said connection lines and belonging to the circuit arrangement.

The second wider opening may then be adapted to tightly surround a light detecting unit with a narrow gap or clearance, wherewith the connection lines of the light detecting unit may be orientated and connected in respect of a board surface or with respect to opposing board surfaces and fastened to connection pads orientated in relation to the connection lines and belonging to the circuit arrangement.

One or more further small channels or openings may be connected to the aperture, said channels or openings being dimensioned to lead or transport a gas flow for the exchange of a first gas portion enclosed in said cavity of the cell with a second gas portion.

Unit-associated electronic circuits are coordinated at least partially with circuits and electrically conductive patterns in the printed circuit board or surface-mounted printed board.

More particularly, the board shall consist of a printed circuit board or a printed circuit board on which components have been surface mounted.

The small slot, channel or aperture in the board shall have high light reflecting properties.

The cover element or cover elements shall also have high light-reflecting properties.

According to one proposed embodiment, the light source may be orientated at right angles to the small slot and/or channel.

In the case of this embodiment, a reflector may be arranged to partially surround the light source and to reflect light beams onto the small slot or the channel.

The small slot and/or the channel will have a width that corresponds to, or essentially to, the width of a coiled incandescent wire.

The small slot or the channel will have a width corresponding, or essentially to, the length of a chosen coiled incandescent wire.

It is also proposed that the small slot or the channel is formed with, or provided with means for concentrating light beams onto a small chip section, located in the light detector.

Advantages

Those advantages that can be considered primarily afforded by the present invention and the special significant characteristic features resides in the creation of conditions which enable a complete gas detecting arrangement to be greatly miniaturized by enabling the measuring path and the cavity of a gas cell arrangement to have the form of a very small slot, a channel or an aperture in a card or board, such as a printed circuit board or a printed circuit board on which components have been surface mounted, while a requisite light source and light detector can be coordinated with and allocated to said board, such as said printed circuit board or component mounted board.

An electronic control unit required by the arrangement can be related, either completely or partially, to a printed circuit board or surface mounted board.

BRIEF DESCRIPTION OF THE DRAWINGS

A previously known arrangement intended and adapted for detecting a gas and/or a gas mixture and a number of proposed embodiments, of the invention at present preferred and having characteristic features significant of the invention, will now be described in more detail by way of example with reference to the accompanying drawings, in which;

FIG. 8 is a sectional view and a side view of the FIG. 2 embodiment of a detector-related embodiment, illustrating a detector-related arrangement, according to the principles of the present invention, applied to a thicker circuit board that comprises a plurality of layers, where a small opening has been given the form of a small channel that includes a bottom surface; and in which;

DESCRIPTION OF PRIOR ART AND PREFERRED EMBODIMENTS

It is pointed out initially that we have chosen to use in the following description of an embodiment that is at present preferred and that includes characteristic features significant of the present invention and illustrated in respective FIGS. 2 to 9 of the accompanying drawings, special terms and terminology with the primary intention of illustrating the inventive concept more clearly.

It will be noted, however, that the expressions chosen here shall not be seen as limited solely to the chosen terms used in the description but that each chosen term shall be interpreted as also including all technical equivalents that function in the same or at least essentially the same way so as to achieve essentially the same purpose and/or the same technical effect.

Figure 1:
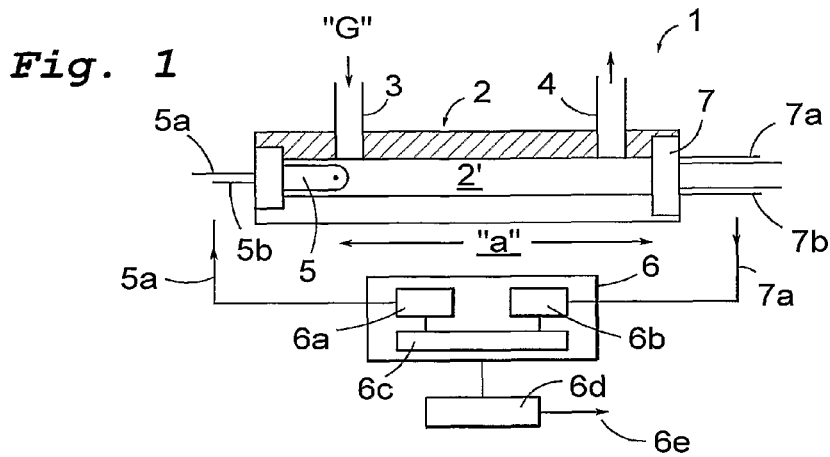
FIG. 1 illustrates the principles of a previously known arrangement intended and adapted for detecting a gas and/or a gas mixture and comprising a light source, a gas cell, a cavity associated with said cell, a light detector and an electronic computing unit.

The fundamental prerequisites of the present invention are illustrated diagrammatically in FIG. 1, illustrating prior art.

This figure illustrates and describes a general embodiment of a gas detecting arrangement 1.

The arrangement 1 can be said to comprise a gas cell 2, that includes a cavity 2' through which a flow of a gas "G" to be evaluated passes.

This is achieved with the aid of a gas inlet 3 and a gas outlet 4 and, when necessary, with the use of a blower (not shown) by means of which associated portions of the gas "G" are forced through the cavity 2'.

The arrangement 1 also includes a light source 5, which is supplied with a pulsating voltage from a controlling and computing unit 6 via a line 5a.

Co-acting with the unit 6 via a line 7a is a light detector 7, which is able to evaluate the electric signal structure that occurs on the light detector 7 time-wise over the line 7a, in accordance with the signal structure initiated time-wise by the light emitter or the light source 5 via a computer equipment or unit 6.

A straight light pulse conducting/measuring path "a" or a path built up by reflection, is provided between the light source 5 and the light detector 7.

In the case of short measuring paths "a" the arrangement 1 is adapted for evaluating the presence of carbon dioxide ($CO_2$) and an existing percentage of the carbon dioxide gas.

The unit 6 is thus adapted for time-wise activation of said light source 5 via a circuit 6a through the line 5a and is also adapted to evaluate the presence of and/or the concentration of gas and/or gas mixture, such as carbon dioxide, enclosed in the cell cavity 2' via circuit 6b, in response to receiving light-detector-related signals from the light detector 7 on the line 7a through the agency of specially constructed circuits 6c.

The calculated result is presented preferably on a display unit 6e related to a circuit 6d.

The circuits in the unit 6 are known in respect of evaluating the presence of and the concentration of gas enclosed in the cavity 2' through the agency of wavelength absorption and will not therefore be described in detail in this document.

The significant units associated with the invention illustrated in the remaining FIGS. 2 to 9 will now be concretised generally with reference to a number of more specifically described embodiments chosen at present.

The present invention is based on the principle of giving the cavity 2' of the gas cell a cross-section which is very small and especially adapted to conform very closely to the outer dimensions of an incandescent filament or wire 5', included in the light source 5.

For the sake of simplicity, the filament 5' will hereinafter be designated as a "light emitting cylinder" that includes an incandescent wire coiled to a diameter "d" and including an incandescent wire coiled to a height "h", wherewith the cavity 2' shall have a width "b" corresponding to the diameter "d" and a depth "c" corresponding to the height "h", in the case of an orientation according to FIGS. 4 and 5.

In the case of this practical application, the width "b" will suitably be only just smaller than the value of the diameter "b" (because of the shadowing risks), although it may, however, slightly exceed the value "d" such as by a factor of up to 2.0, normally by a factor of up to 1.5, although during an increase in the volume of the cavity 2'.

For similar reasons, the depth measurement "c" will preferably be scarcely smaller than the value of the height "h", but may exceed the value "h" such as by a factor of up to 1.5, usually of a factor by up to 1.2 although during an increase of volume in the cavity 2'.

A fundamental feature is also that the space angle used to transporting light from the light source 5 to the light detector 7 shall include at least those light beams that are directed along the cavity 2' and also those beams that pass obliquely into the elongate form of the small cavity 2' and that can be reflected by the wall portions of the cavity.

This concerns primarily the opposing parallel, or generally parallel, surfaces, such as plane-parallel surfaces belonging to the sectional surfaces of the component-mounted circuit board that form the cavity 2', which may be treated to provide the effective light-reflecting properties in a known fashion.

Secondly the element or lid 12, covering the small cavity 2', may be treated to provide said effective light-reflecting properties.

By dimensioning the cavity 2' or by means of other cavity-related measures, the light beams passing through the small cavity 2' shall be concentrated to a heat-absorbing chip section 7' formed in the light detector 7.

However, also lying within the scope of the present invention are different measures for directing light beams within further space angles from the light emitter or light source 5 and its incandescent wire 5' to the narrow cavity 2', which is described in more detail hereinafter with reference to the embodiment illustrated in FIG. 6.

Figure 2:
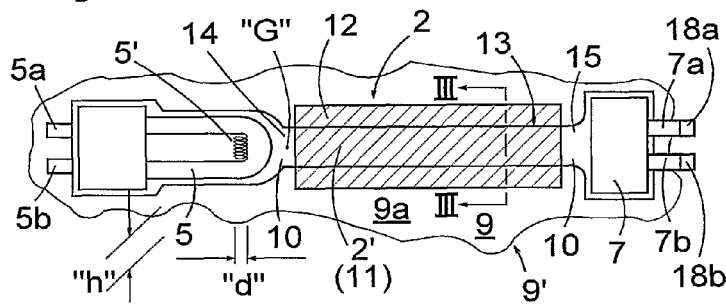
FIG. 2 is a horizontal view illustrating a first embodiment of a detector-related arrangement, according to the present invention, which, although not shown, includes a computing unit applied to a thin surface mounted board that includes a few layers.
Figure 3:
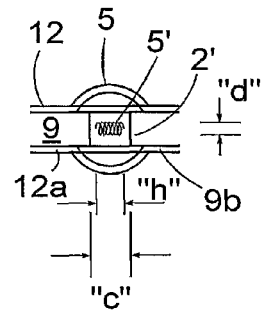
FIG. 3 is a sectional view of the embodiment shown in FIG. 2, taken along lines III-III.
Figure 4:
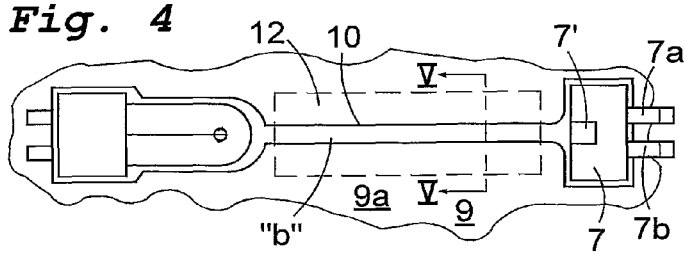
FIG. 4 is a horizontal view of a second embodiment of a detector-related arrangement, in accordance with the present invention, which includes (although not shown) a computing unit applied to a thin printed circuit board that comprises only a few layers.
Figure 5:
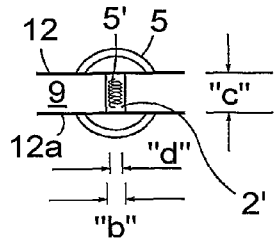
FIG. 5 is a sectional view of the embodiment shown in FIG. 4 taken along lines V-V in FIG. 4.

In view of the form of the light emitting "cylinder", having a diameter "d" and a height "h", a cavity-forming aperture, in the form of a small slot 10 in FIGS. 2 and 3, can be orientated along the upper surface 9a of the board or card 9, or, as illustrated in FIGS. 4 and 5, orientated in the form of a small slot 10 at right angles to the upper surface 9a of the board or card 9.

However, there is nothing that prevents the small slot 10 of FIGS. 4 and 5 from having a through-penetrating structure and therewith given a pronounced square cross-section, although this might result in a cavity 2' of unnecessary large volume.

According to the embodiments, illustrated in the FIGS. 2 to 7, the gas cell 2 and its cavity 2' in the arrangement 1 are structured within a short section 9 as a through-penetrating small slot or opening 10.

Figure 8:
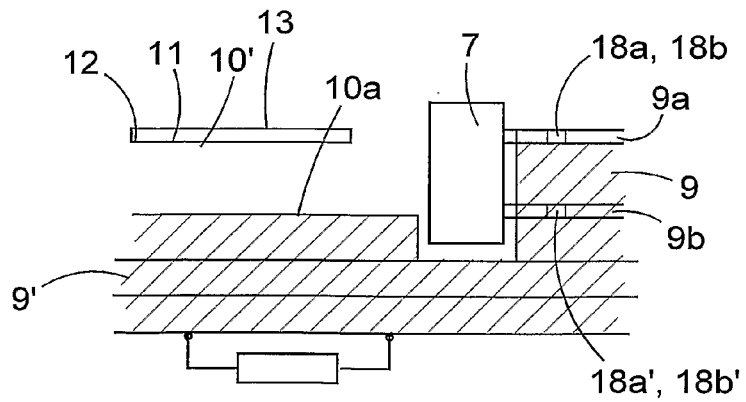
Figure 9:
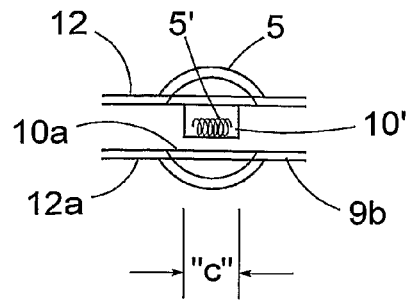
FIG. 9 illustrates a supplemented embodiment, according to FIG. 3, where an opening or recess has been given the form of a small channel that includes a bottom surface.

By way of an alternative, FIGS. 8 and 9 illustrate the use of an opening 10' in the form of a small channel that has a bottom part 10a in the board 9' or in the surface mounted board 9.

The slot or the channel 10 and/or the upper opening 11 of said channel or aperture 10' in said board 9' or said surface-mounted board 9 is/are covered by a lid-functioning element, a first element 12, applied to the surface 9a, and a second element 12a applied to the surface 9b.

In FIGS. 2 to 7 the aperture in the form a small slot 10 is structured to pass completely through the card or board 9 with the lid-functioning element 12 and 12a placed on one side 9a or on both sides 9a, 9b of the card or board 9.

Each of the lid-functioning elements 12, 12a may have the form of an elongate piece of adhesive tape 13 with an adhesive layer 13a, 13b on one side 9a of the card or board 9 and including at least one intermediate section 13c.

The small slot 10 or channel 10' is connected directly to a first wider opening 14 related to the light source 5.

The small slot 10 or channel 10' is also connected directly to a second wider opening 15 related to the light detector 7.

Figure 7:
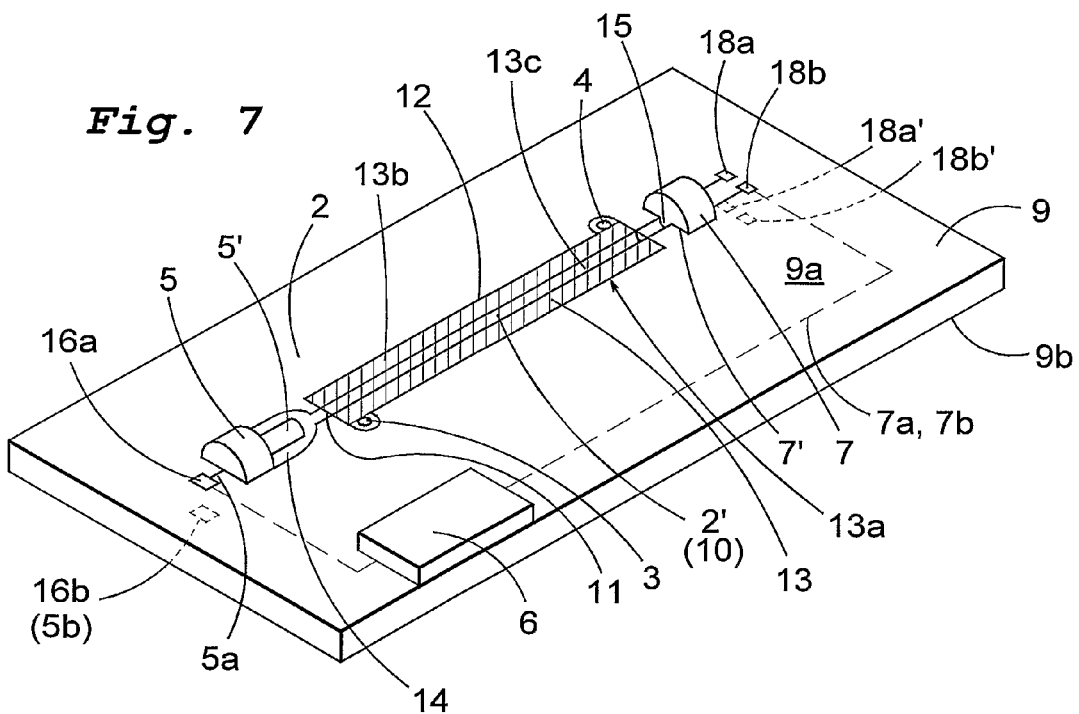
FIG. 7 illustrates in perspective the manufacture of part of a thin surface-mounted circuit board on which the light source and the light detector have been placed in wider end-related recesses in relation to a small straight cavity or slot.

In the case of the embodiments, illustrated in FIG. 2 and in FIG. 7, the first wider opening 14 is adapted to only slightly surround a standard light-emitting source 5, whose two connecting lines 5a, 5b are orientated with regard to one surface 9a of the board, or may, conveniently, be orientated with regard to each of its opposing surfaces 9a, 9b of the board and fastened to connecting pads 16a, 16b orientated with respect to said connecting lines, wherein said pads 16a, 16b can both be placed on the upper surface 9a or on the surface 9a and on the surface 9b depending on the placement of the light source 5.

The second wider opening 15 is adapted to surround a light detecting unit 7, whose two connecting lines 7a, 7b are orientated with regard to a board surface 9a and are connected to said lines with the aid of connecting pads 18a, 18b orientated with respect to said lines.

A light detecting unit 7 will normally include two further connecting lines (not shown) that can be connected to connection pads 18a' and 18b' on the opposing surface of the board.

One or more further channels or openings 3, 4 are connected to said slot 10 or said channel 10' for conducting gas "G" for replacement of a first gas portion in said gas cell with a second gas portion.

Electronic circuit 6a, 6b, 6c belonging to said unit are coordinated at least partially with circuits and patterns belonging to said circuit board 9.

FIGS. 4 and 5 illustrate another embodiment of the invention, in which the slot 10 is narrower and deeper than the slot in the embodiment shown in FIGS. 2 and 9, and has a width "b" corresponding to the diameter of the incandescent wire 5' and where the light beams are concentrated to the heat sensitive chip section 7' on the light detector 7, this embodiment being particularly recommended.

Figure 6:
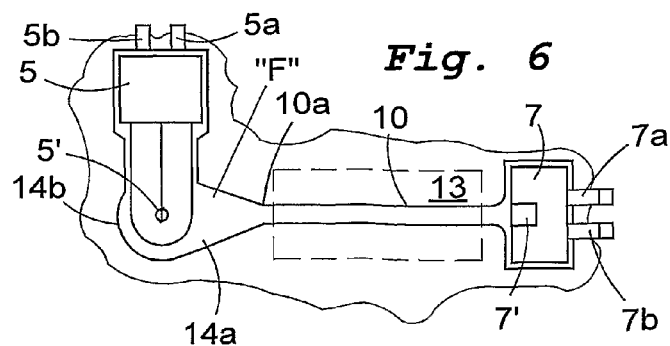
FIG. 6 is a horizontal view that illustrates a detector-related arrangement of a third embodiment, according to the present invention, which includes (although not shown) a computing unit applied to a thin circuit board that includes only or a few layers.

FIG. 6 illustrate a case in which the light source 5 and the incandescent wire 5' are orientated at right angles to the slot 10 (see FIGS. 4 and 5) where the aperture 14a is formed as reflector 14b to concentrate light beams from a larger space angle essentially with a focusing point "F" located in or immediately adjacent to the end region 10a of the small slot 10.

It is known to form light reflectors for this end and will not therefore be described in detail in this document.

Detection of the presence of $CO_2$-gas, in a concentration of up to 20%, will normally require a small and narrow measuring path "a" of about 2 to 4 mm, whereas a concentration of up to 5% will normally require a measuring path of about 8 to 16 mm.

The cylindrical light source 5 consisting of coiled incandescent wire 5' may be considered to have a diameter "d" of about 0.2 to 0.5 mm, whereas the cylinder may have a chosen height "h" of up to about 8 to 12 mm.

Although the slot 10 and the channel 10' of the embodiment described above are said to be straight, it will be understood that the slots and channels may be arcuate in shape or have other shapes and include light reflecting properties so as to fulfill the aims of the present invention.

Although a tape 13 is shown to extend between the light source 5 and the light detector 7 it will be understood that a wider and longer section of tape 13 can be used so as to cover both the light source and/or the light detector 7.

It will also be understood that the invention is not limited to the exemplifying embodiments described above and that modifications and variations can be made within the framework of the concept of the invention illustrated in the accompanying claims.

It will be noted in particular that each described unit and/or circuit can be combined with each other shown unit and/or circuit within the framework of achieving intended technical functions.

The invention claimed is:

1. A gas detecting arrangement that comprises
a gas cell, which includes
a cavity formed in a circuit board with a gas inlet and a gas outlet,
a gas-cell related light source disposed in the circuit board at a first end of the cavity,
a gas-cell related light detector disposed in the circuit board at a second end of the cavity, and
a controlling and computing unit disposed adjacent the cavity on a surface of the circuit board, the controlling and computing unit being adapted for initiating activation of said light source and also adapted to evaluate the presence of and/or the concentration of a gas and/or a gas mixture enclosed in the cell cavity in response to receiving light-detector-signals from the light detector,
wherein said cavity is structured as at least one of a small aperture, a small slot, or a small channel with a dimension generally corresponding to a dimension of the light source; and
wherein an opening provided in said board and related to the aperture slot, or channel, is covered with a lid functioning element.

2. An arrangement according to claim 1, wherein said channel is structured to pass completely through said board and in that said lid-functioning element can be placed on one or both sides of the board.

3. An arrangement according to claim 1, wherein said lid-functioning element is comprised of adhesive tape.

4. An arrangement according to claim 1, wherein at least one of said aperture, slot, and channel is connected directly to a first wider opening relating to the light source.

5. An arrangement according to claim 1, wherein at least one of said aperture, slot, and channel is connected directly to a second wider opening relating to the light detector.

6. An arrangement according to claim 4, wherein the first wider opening is adapted to surround a light emitting unit or a light source, whose connection lines are orientated in relation to a board surface or in relation to opposing board surfaces and fastened to connection pads orientated in relation to said connection lines.

7. An arrangement according to claim 5, wherein said second wider opening is adapted to surround a light detecting unit, whose connection lines are orientated in relation to a board surface and in relation to opposing board surfaces and connected to connection pads orientated in relation to said connection lines.

8. An arrangement according to claim 1, wherein at least one of said aperture, slot, and channel is also connected to one or more further channels or apertures adapted for conducting transportation of a gas or a gas flow for replacement of a first gas portion in said gas cell with a second gas portion.

9. An arrangement according to claim 1, wherein electronic circuits belonging to said unit are co-ordinated, at least partially, with circuits and patterns belonging to said board.

10. An arrangement according to claim 1, wherein said board is a printed circuit board or a circuit board on which components have been mounted.

11. An arrangement according to claim 1, wherein the aperture, slot, or channel provided in said board has high light-reflecting properties.

12. An arrangement according to claim 1, wherein the lid-functioning element has high light-reflecting properties.

13. An arrangement according to claim 1, wherein said light source extends at right angles to said aperture, slot, and/or channel.

14. An arrangement according to claim 13, wherein said circuit board further comprises a reflector which is adapted to reflect light beams onto the aperture, the slot, or channel.

15. An arrangement according to claim 1, wherein at least one of said aperture, channel, and slot has a width corresponding to, or generally corresponding to, the width of a coiled incandescent element.

16. An arrangement according to claim 1, wherein at least one of said aperture, slot, and channel has a width corresponding to, or at least generally to, the length of a coiled incandescent element.

17. An arrangement according to claim 1, wherein at least one of said aperture, slot, and channel are formed with or provided with means for concentrating the light beams onto a chip section in the light detector.

* * * * *